(12) United States Patent
Pickersgill et al.

(10) Patent No.: US 7,671,191 B2
(45) Date of Patent: Mar. 2, 2010

(54) METHODS FOR PREPARING 2-ALKYNYLADENOSINE DERIVATIVES

(75) Inventors: Iain F. Pickersgill, Newtown, PA (US); Edward H. Cheesman, Lunenburg, MA (US)

(73) Assignee: PGx Health, LLC, Newton, MA (US)

( * ) Notice: Subject to any disclaimer, the term of this patent is extended or adjusted under 35 U.S.C. 154(b) by 14 days.

(21) Appl. No.: 11/975,080

(22) Filed: Oct. 17, 2007

(65) Prior Publication Data
US 2008/0177055 A1 Jul. 24, 2008

Related U.S. Application Data

(63) Continuation of application No. 10/848,403, filed on May 18, 2004, now abandoned.

(60) Provisional application No. 60/471,643, filed on May 19, 2003.

(51) Int. Cl.
*C07H 21/00* (2006.01)
(52) U.S. Cl. ............... 536/25.3; 536/18.5; 536/18.6
(58) Field of Classification Search ............... None
See application file for complete search history.

(56) References Cited

U.S. PATENT DOCUMENTS

| | | | |
|---|---|---|---|
| 4,956,345 | A | 9/1990 | Miyasaka et al. |
| 5,140,015 | A | 8/1992 | Olsson et al. |
| 5,278,150 | A | 1/1994 | Olsson et al. |
| 5,593,975 | A | 1/1997 | Cristalli |
| 5,877,180 | A | 3/1999 | Linden et al. |
| 6,117,878 | A | 9/2000 | Linden |
| 6,232,297 | B1 | 5/2001 | Linden et al. |
| 6,322,771 | B1 | 11/2001 | Linden et al. |
| 6,326,359 | B1 | 12/2001 | Monaghan et al. |
| 6,350,735 | B1 | 2/2002 | Monaghan |
| 6,448,236 | B1 | 9/2002 | Monaghan |

FOREIGN PATENT DOCUMENTS

| | | |
|---|---|---|
| EP | 0 219 876 B1 | 4/1987 |
| EP | 0 267 878 A1 | 5/1988 |
| EP | 0 277 917 A2 | 8/1988 |
| EP | 0 309 112 B1 | 3/1989 |
| EP | 0 323 807 A2 | 7/1989 |
| GB | 2 203 149 A | 10/1988 |
| WO | WO 99/61054 | 12/1999 |
| WO | WO 00/44763 | 8/2000 |
| WO | WO 00/78774 A2 | 12/2000 |
| WO | WO 03/029264 A2 | 4/2003 |
| WO | WO 03/029264 A3 | 4/2003 |

OTHER PUBLICATIONS

Goodnow et al. Tetrahedron Letters (1997), vol. 38, pp. 3195-3198.*
Agrofoglio et al. Chem. Rev. (2003), vol. 103, pp. 1875-1916.*
Belardinelli, J., et al.., "The cardiac effects of adenosine," Progress in Cardiovasc. Dis., 1989, 32(1), 73-97.
Bruns, R.F., et al., "Characterization of the A2 adenosine receptor labled by [3H] NECA in rat striatal membranes," Mol. Parmacol., 1986, 29(4), 331-336 (PubMed abstract, downloaded Aug. 20, 2004.
Cristalla, G., et al. "2-Alkynyl derivatives of adenosine and adenosine-5' -N- ethyluronamide as selective agonists at A2 adenosine receptors,"J. Med.Chem., 1992, 35, 2363-2368.
Daly, J.W., "Adenosine receptors: targets for future drugs," J. Med. Chem., 1982, 25(3), 197-207.
Epp, J.B., et al., "Facile preparation of nucleoside-5' -carboxylic acids," J. Org. Chem., 1999, 64, 293-295.
Homma, H., et al., "Nucleosides and nucleotides. 112 2-(hexyn-1-yl) adenosine-5'uronamides: A new entry of selective A2 adenosine receptor agonists with potent antihypertensive activity," J. Med. Chem., 1992, 35, 2881-2890.

(Continued)

*Primary Examiner*—Patrick T Lewis

(57) ABSTRACT

Disclosed are methods for preparing 2-alkynyladenosine derivatives of formula A:

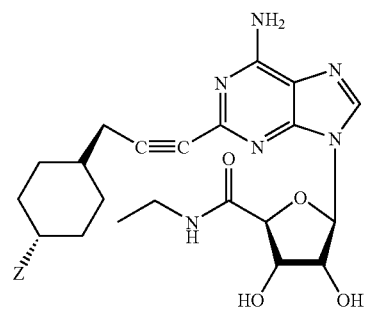

or a stereoisomer, pharmaceutically acceptable salt, hydrate, solvate, acid salt hydrate or isomorphic crystalline form thereof, the method comprising the step of:
contacting 2-iodoadenosine-5'-N-ethyluronamide with a compound of formula B:

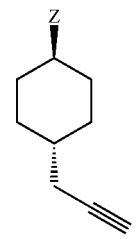

wherein Z is —C(═O)OR or —CH$_2$C(═O)R, where R is a C$_1$ to C$_5$ alkyl, preferably The methods are useful for preparing 2-alkynyladenosine derivatives that are, in certain embodiments, adenosine receptor agonists.

10 Claims, No Drawings

OTHER PUBLICATIONS

Hundertmark, T., et al., "Pd(PhCN)2Cl2/P(t-Bu)3: A versatile catalyst for sonogashira reactions of aryl bromides at room temperatures," Am. Chem.Soc., 2000, 2(12), 1729-1731.

Jacobson, K.A., et al., "Adenosine receptors: pharmacology, structure-activity relationships, and therapeutic potential," J. Med. Chem., 1992, 35(3), 407-422.

Jarvis, et al., J. Pharmacological and Experimental Therapeutics, 1989, 251(3) 888-893 (JPET—Anstract).

Matsuda, A., et al., "Nucleosides and nucleotides. 103. 2-alkynyladenoaines; a novel class of selective adenosine A2 receptor agonists with potent antihypertensive effect," J. Med. Chem., 1992, 35, 241-252.

Nair V., et al., "Modification of nucleic acid bases via radical intermediates: synthesis of dihalogenated purine nucleosides," Synthesis, 1982, 670-672.

Olsson, R.A., et al., "Cardiovascular purinoceptors," Physiol. Rev., 1990, 70 (3), 761-845.

Rieger, J.M., et al., "Design, synthesis, and evaluation of novel A2a adenosine receptor agonists," J. Med. Chem., 2001, 44, 531-539.

Stone, T.W., "Purine receptors and their pharmacological Roles," Advances in Drug Res., Academic Press Ltd., 1989, 18, 291-429.

Malachowski, R., et al., "Tests in the cyclohexane group," Chem. Ber., 1938, 71(4), 759-767.

\* cited by examiner

METHODS FOR PREPARING 2-ALKYNYLADENOSINE DERIVATIVES

CROSS REFERENCE TO RELATED APPLICATIONS

This application is a continuation of U.S. application Ser. No. 10/848,403, filed May 18, 2004 now abandoned, which claims the benefit of U.S. Provisional Application No. 60/471,643, filed May 19, 2003, the entire contents of which are incorporated herein by reference.

FIELD OF THE INVENTION

This invention relates to improved methods for preparing 2-alkynyladenosine derivatives, more specifically, to improved methods for preparing 2-alkynyladenosine derivatives that are, in certain embodiments, adenosine receptor agonists and, even more specifically, to improved methods for preparing 2-alkynyladenosine derivatives that are, in certain embodiments, $A_2$ adenosine receptor agonists.

BACKGROUND OF THE INVENTION

Adenosine is known to modulate a number of physiological functions. At the cardiovascular system level, adenosine is strong vasodilator and cardiac depressor. In the central nervous system, adenosine induces sedative, anxiolytic and antiepileptic effects. At the kidney level, it exerts a diphasic action, inducing vasoconstriction at low concentrations and vasodilation at high doses. Adenosine acts as a lipolysis inhibitor on fat cells and as an anti-aggregant on platelets (Stone T. W., Purine Receptors and their Pharmacological Roles, *Advances in Drug Research*, Academic Press Limited, 1989, 18, 291-429; *Progress Cardiovasc. Dis.* 1989, 32, 73-97).

A number of studies have shown that adenosine actions are mediated by two subtypes of receptors that are located on the cell membrane: one of high-affinity, inhibiting the activity of the enzyme adenylate cyclase ($A_1$ receptor), and another of low-affinity, stimulating the activity of the same enzyme ($A_2$ receptor). (*J. Med. Chem.* 1982, 25, 197-207; *Physiol. Rev.* 1990, 70(3), 761-845; *J. Med. Chem.* 1992, 35, 407-422). Both receptors are widely spread in the different systems of the organism. In some tissues, however, only one of said receptors is mainly present. For example, the $A_1$ receptor is more prevalent than the $A_2$ receptor at the cardiac level, whereas the $A_2$ receptor is more prevalent than the $A_1$ receptor at the vascular level and on platelets.

Compounds capable of interacting selectively with either the $A_1$ or $A_2$ receptor could have an interesting pharmacological pattern. Furthermore, the vasodilating activity, together with the anti-aggregating action, of the compounds that interact with the $A_2$ receptors may lead to useful therapeutic applications in the treatment of severe cardiovascular pathologies, such as ischemic cardiopathy, hypertension and atherosclerosis. Moreover, due to the actions on central nervous system, the use of $A_2$ selective medicaments can be envisaged in the treatment of cerebrovascular ischemia, epilepsy and various emotional disorders, such as anxiety and psychosis.

Previously, adenosine-5'-N-ethyluronamide or NECA (*Mol. Pharmacol.*, 1986, 25, 331-336) was the only known compound, other than adenosine, having agonist activity at the $A_2$ receptor. Unfortunately, NECA is also active on the $A_1$ receptor and thus lacks specificity for the $A_2$ receptors alone. Because it was the only available compound having $A_2$ affinity, NECA was used for pharmacological tests for the receptor binding.

More recently, however, certain NECA derivatives having $A_2$ receptor selectivity have been developed. These compounds are NECA derivatives that are substituted at the C2-position with phenylamino groups. For example, the compound 2-(p-(carboxyethyl)phenylethylamino)-5'-N-ethyluronamide, named CGS 21680 (*J. Pharmacol Exp. Ther.*, 1989, 251, 888-893), has become the reference compound for the pharmacological studies on $A_2$ receptor.

Other purine derivatives having selective $A_2$ agonist activity are disclosed, for example, in GB-A-2203149; EP-A-0309112; EP-A-0267878; EP-A-0277917; and EP-A-0323807. Substitution at the 2-position of the purine group has been considered promising to give the desired selectivity (*J. Med. Chem.* 1992, 35, 407-422). 2-Alkynylpurine derivatives have been disclosed in EP-A-0219876 and U.S. Pat. No. 4,956,345.

U.S. Pat. No. 5,593,975 discloses 2-alkynyl adenosine derivatives substituted at the ethyne position with aryl, heterocyclic or hydroxyalkyl groups and in which the riboside residue is substituted by the N-alkyl- (or cycloalkyl)-uronamido. It is reported that these compounds exhibit strong $A_2$ agonist selectivity and, therefore, are useful for the treatment of cardiovascular pathologies, such as cardiac ischemia, hypertension and atherosclerosis and of diseases of the central nervous system, such as cerebrovascular ischemia, epilepsy and emotional disorders (anxiety and psychosis).

The 2-alkynyl adenosine derivatives of U.S. Pat. No. 5,593,975 have the following general formula:

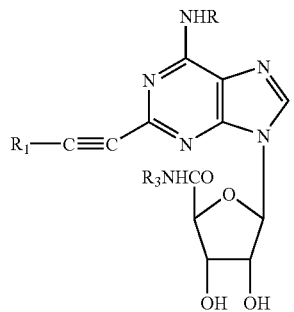

I wherein R is hydrogen, $C_1$-$C_6$ alkyl, $C_3$-$C_7$ cycloalkyl, phenyl $C_1$-$C_3$ alkyl;

wherein $R_1$ has one of the following meanings:

(a) phenyl or naphthyl optionally substituted with one to three halogen atoms (chlorine, fluorine or bromine), $C_1$-$C_6$ alkyl, $C_1$-$C_6$ haloalkyl, $C_1$-$C_6$ alkoxy, $C_1$-$C_6$ haloalkoxy, $C_2$-$C_6$ alkoxycarbonyl, $C_2$-$C_6$ alkoxyalkyl, $C_1$-$C_6$ alkylthio, thio, CHO, cyanomethyl, nitro, cyano, hydroxy, carboxy, $C_2$-$C_6$ acyl, amino, $C_1$-$C_3$ monoalkylamino, $C_2$-$C_6$ dialkylamino, methylenedioxy; or aminocarbonyl;

(b) a group of the formula —$(CH_2)_m$-Het wherein m is 0 or an integer from 1 to 3 and Het is 5 or 6 membered heterocyclic aromatic or non aromatic ring, optionally benzocondensed, containing 1 to 3 heteroatoms selected from oxygen, nitrogen or sulphur, linked through a carbon atom or through a nitrogen atom;

(c) $C_3$-$C_7$ cycloalkyl optionally containing unsaturations or $C_2$-$C_4$ alkenyl;

(d) moieties of the following formula:

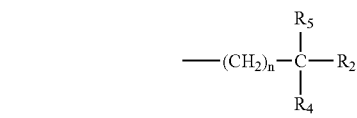

where $R_2$ is hydrogen, methyl or phenyl;

$R_4$ is OH, $NH_2$, dialkylamino, halogen, or cyano;

$R_5$ is hydrogen, $C_1$-$C_6$ linear or branched alkyl, $C_5$-$C_6$ cycloalkyl or $C_3$-$C_7$ cycloalkenyl, phenyl-$C_1$-$C_2$-alkyl or $R_2$ and $R_5$, taken together, form a 5 or 6-membered carbocyclic ring or $R_3$ is hydrogen and $R_2$ and $R_4$, taken together, form an oxo group or a corresponding acetalic derivative;

when R is different from hydrogen and/or $R_3$ is different from ethyl, $R_1$ can also be $C_1$-$C_6$ linear or branched alkyl; and n is 0 or 1 to 4; and wherein $R_3$ is $C_1$-$C_6$ alkyl, $C_3$-$C_7$-cycloalkyl, phenyl or benzyl; provided that when R is different that hydrogen or when R is hydrogen and $R_3$ is cyclopentyl, phenyl or benzyl, $R_1$ can also be $C_1$-$C_6$ linear or branched alkyl.

The 2-alkynyl adenosine compounds of U.S. Pat. No. 5,593,975 are prepared by the general synthetic schemes shown below.

SCHEME I

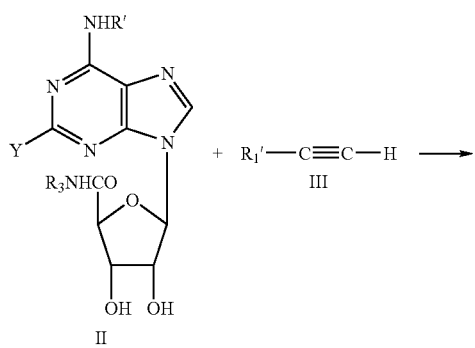

SCHEME II

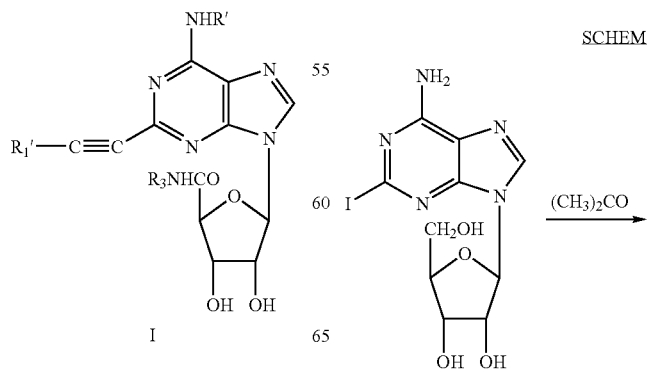

In schemes I and II, R' and $R'_1$ have the same meanings as R and $R_1$, respectively, or they are groups which can be converted into R and $R_1$, respectively, for example, by removing any protecting groups which can be present in R' and $R'_1$ compatible with the reaction conditions; Y is Br or I and X is chlorine, bromine or iodine.

The reactions shown in schemes I and II are carried out in the presence of catalysts (for example: bis(triphenylphosphine) palladium dichloride and a cuprous halide) and a suitable acid-binding agent, such as an organic base (for example: triethylamine, diisopropylethylamine or pyridine).

As the solvent, a substituted amide (such as dimethylformamide), an ether (such as dioxane or tetrahydrofuran), acetonitrile or optionally a mixture of two or more of said solvents, are preferably used.

The compounds of formula II, in which Y is iodine and R' is hydrogen, can be prepared from 2-iodoadenosine (Nair et al., *Synthesis*, 1982, 670-672) according to the following Scheme III:

SCHEME III

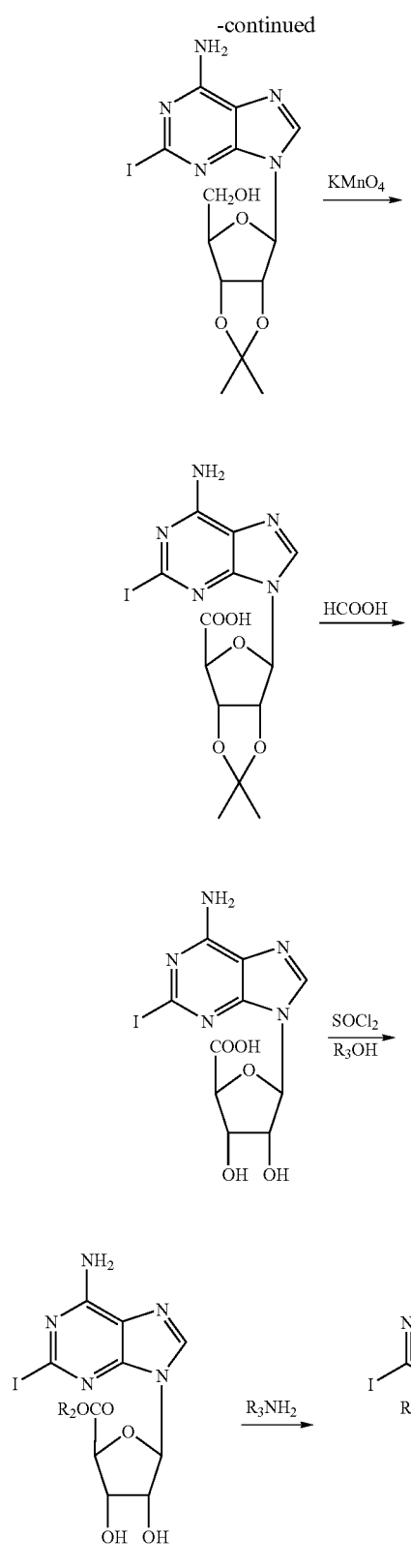
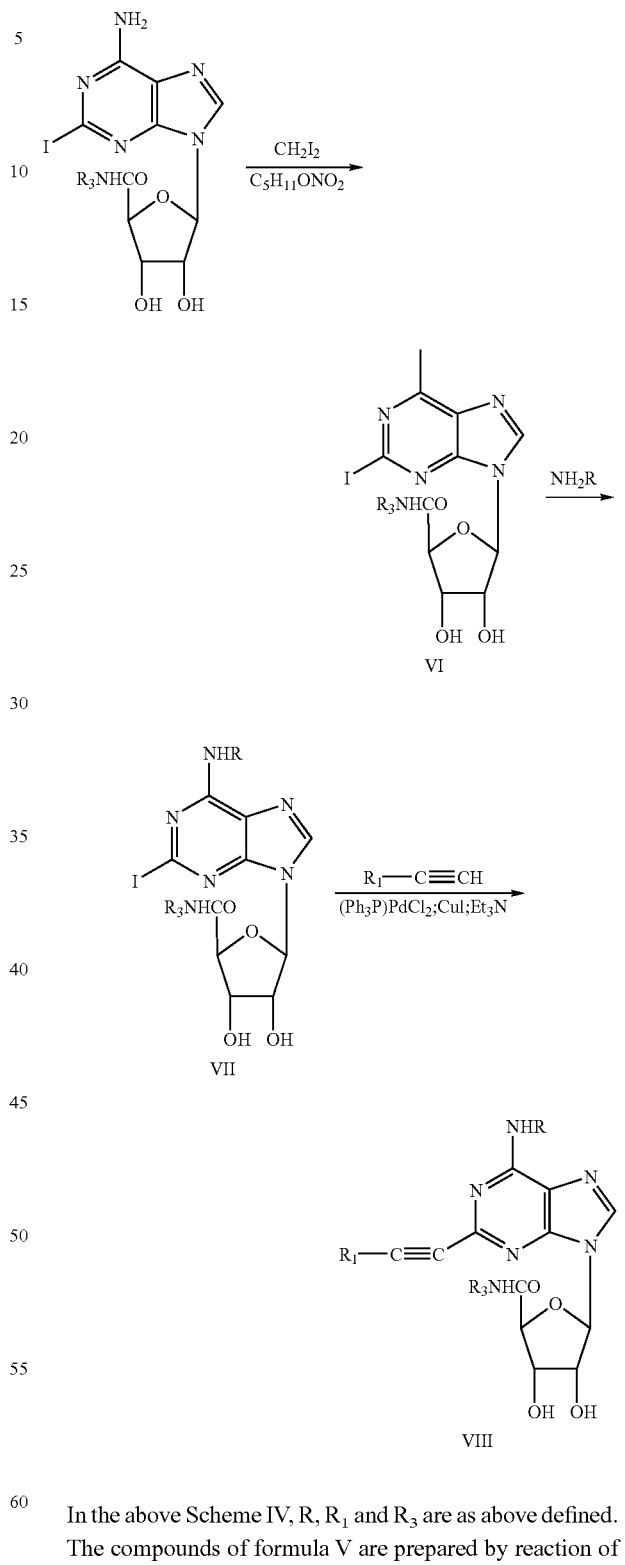

Compounds of formula VIII in which Y is iodine and R' is different from hydrogen can be prepared according to the following Scheme IV:

In the above Scheme IV, R, $R_1$ and $R_3$ are as above defined.

The compounds of formula V are prepared by reaction of compounds of formula II with an acetylene derivative, for example, 1-trimethylsilylacetylene, under the conditions reported for the reaction between compounds II and III. Compounds III and IV are known or they can be prepared according to well-known methods.

U.S. Pat. No. 6,322,771 discloses compounds of formula IX:

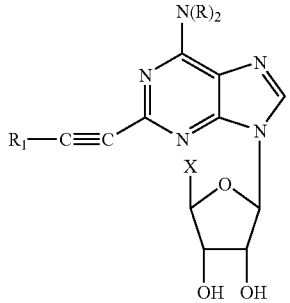

(IX)

wherein
(a) each R is individually hydrogen, $C_1$-$C_6$ alkyl, $C_3$-$C_7$ cycloalkyl, phenyl or phenyl($C_1$-$C_3$)-alkyl;
(b) X is —$CH_2OH$, —$CO_2R^2$, —$OC(O)R^2$, —$CH_2OC(O)R^2$ or —$C(O)NR^3R^4$;
(c) each of $R^2$, $R^3$ and $R^4$ is individually H, $C_1$-$C_6$-alkyl; $C_1$-$C_6$-alkyl substituted with 1-3 $C_1$-$C_6$ alkoxy, $C_{3-7}$cycloalkyl, $C_1$-$C_6$-alkylthio, halogen, hydroxy, amino, mono($C_1$-$C_6$-alkyl)amino, di($C_1$-$C_6$-alkyl)amino, or $C_6$-$C_{10}$-aryl, wherein aryl may be substituted with 1-3 halogen, $C_1$-$C_6$-alkyl, hydroxy, amino, mono($C_1$-$C_6$-alkyl)amino, or di($C_1$-$C_6$-alkyl)amino; $C_6$-$C_{10}$-aryl; or $C_6$-$C_{10}$-aryl substituted with 1-3 halogen, hydroxy, amino, mono($C_1$-$C_6$-alkyl)amino, di($C_1$-$C_6$-alkyl) amino, or $C_1$-$C_6$-alkyl; and
(d) $R^1$ is (X—(Z)—)$_n$[($C_3$-$C_{10}$)cycloalkyl]-(Z')— wherein Z and Z' are individually ($C_1$-$C_{10}$)alkyl, optionally interrupted by 1-3 S or nonperoxide O, or is absent, and n is 1-3.

It is disclosed that the compounds of Formula IX may be prepared by the synthetic methods disclosed in U.S. Pat. Nos. 5,278,150; 5,140,015; 5,877,180; 5,593,975; and 4,956,345.

U.S. Pat. No. 6,322,771 discloses preferred compounds of Formula IX, wherein each R is H, X is ethylaminocarbonyl and $R^1$ is 4-carboxycyclohexylmethyl (DWH-146a), $R^1$ is 4-methoxycarbonylcyclohexylmethyl (DWH-146e) or $R^1$ is 4-acetoxymethyl-cyclohexylmethyl (JMR-193):

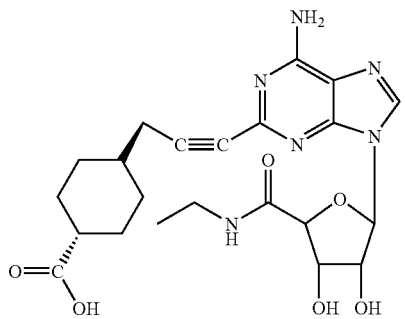

DWH-146a

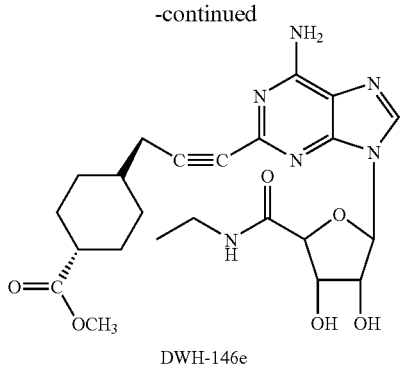

DWH-146e

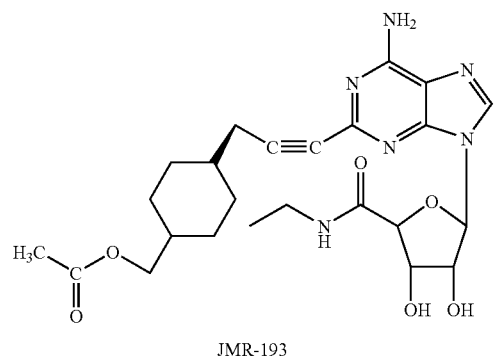

JMR-193

According to U.S. Pat. No. 6,322,771, the synthesis of the methyl 4[3-(6-amino-9(5-[(ethylamino)carbonyl]-3,4-dihydroxytetrahydro-Z-furanyl-9H-2-purinyl)-2-propynyl]-1-cyclohexanecarboxylate (DWH-146e) was accomplished by the cross coupling of an iodo-adenosine derivative (N-ethyl-1'-deoxy-1'-(amino-2-iodo-9H-purin-9-yl)-β-D-ribofuranuoramide) with methyl 4-(2-propynyl)-1-cyclohexanecarboxylate by utilization of a Pd(II) catalyst.

The iodo-adenosine derivative was first prepared from guanosine by treating it with acetic anhydride, which acetylates the sugar hydroxyls. The resulting compound was then chlorinated at position 6 with tetramethyl ammonium chloride and phosphorous oxychloride. Iodination of position 2 was accomplished via a modified Sandmeyer reaction, followed by displacement of the 6-Cl and sugar acetates with ammonia. The 2' and 3' hydroxyls were protected as the acetonide and the 5' hydroxyl was oxidized to the acid with potassium permanganate. Deprotection of the 2' and 3' acetonide, Fisher esterification of the 5' acid with ethanol and conversion of the resulting ethyl ester to the ethyl amide with ethylamine gave N-ethyl-1'-deoxy-1'-(amino-2-iodo-9H-purin-9-yl)-β-D-ribofuranuoramide.

The acetylene [methyl 4-(2-propynyl)-1-cyclohexanecarboxylate] was synthesized starting from trans-1,4-cyclohexanedimethanol. Initially, the trans-diol was monotosylated followed by displacement of the tosylate with an acetylene anion. The hydroxyl of the resulting hydroxyl acetylene species was oxidized to the acid via Jones reagent followed by methylation with (trimethylsilyl)diazomethane to give methyl 4-(2-propynyl)-1-cyclohexanecarboxylate.

A cross-coupling reaction of N-ethyl-1'-deoxy-1'-(amino-2-iodo-9H-purin-9-yl)-β-D-ribofuranuoramide and methyl 4-(2-propynyl)-1-cyclohexanecarboxylate was then performed. To a solution of N,N-dimethylformamide (0.5 mL), acetonitrile (1 mL), triethylamine (0.25 mL), and N-ethyl-1'-deoxy-1'-(amino-2-iodo-9H-purin-9-yl)-β-D-ribofuranuroamide (25 mg, 0.06 mmol) was added bis(triphenylphosphine) palladium dichloride (1 mg, 2 mol %) and copper(I) iodide (0.06 mg, 0.5 mol %). To the resulting mixture was added methyl 4-(2-propynyl)-1-cyclohexanecarboxylate (54 mg, 0.3 mmol) and the reaction was stirred under nitrogen atmosphere for 16 hours. The solvent was removed under vacuum and the resulting residue was flash chromatographed in 20% methanol in chloroform ($R_f$=0.45) to give 19 mg (off-white solid, mp 125° C. (decomposed)) of 4[3-(6-amino-9(5-[(ethylamino)carbonyl]-3,4-dihydroxytetrahydro-Z-furanyl)-9H-2-purinyl)-2-propynyl]-1-cyclohexanecarboxylate (DWH-146e).

These above-described synthetic methods for producing 2-alkynyladenosine derivatives, including DWH-146e, provide lower yields than desired, require prolonged reaction times and require extensive chromatographic purification. For example in U.S. Pat. No. 5,593,975, the acetonide protection (first step of Scheme III above) requires purification by column chromatography. Furthermore, the oxidation procedure (second step of Scheme III above) requires prolonged reaction times and has been noted to be troublesome due to competing oxidation at the 2-iodo position. Homma et al., *J. Med. Chem.*, 1992, 35, 2881-2890. In U.S. Pat. No. 6,322,771, the first step of the synthesis of the cyclohexane-containing acetylene requires purification by column chromatography to separate the desired mono-tosyl product from the starting diol and bis-tosyl products. In the second step of the synthesis of the cyclohexane-containing acetylene, prolonged reaction times, a large excess of the acetylene anion and purification by column chromatography are required. Furthermore, the cross-coupling reaction between the cyclohexane-containing acetylene and 2-iodoNECA proceeds with poor yield after chromatography.

Thus, there is a need for improved synthetic methods for producing 2-alkynyladenosine derivatives that provide higher yields and require less purification than prior art methods. Using alternative reagents and steps, we have discovered an improved method for producing 2-alkynyladenosine derivatives at higher yields with less chromatographic purification required.

SUMMARY OF THE INVENTION

In one embodiment, the invention is directed to methods for preparing compounds of formula A:

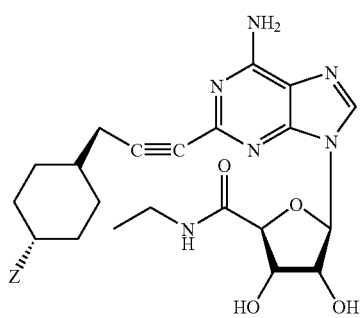

or a stereoisomer, pharmaceutically acceptable salt, hydrate, solvate, acid salt hydrate or isomorphic crystalline form thereof the method comprising the step of:

contacting 2-iodoadenosine-5'-N-ethyluronamide with a compound of formula B:

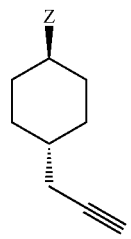

wherein Z is —C(═O)OR or —CH$_2$OC(═O)R, where R is a C$_1$ to C$_5$ alkyl, preferably methyl.

The invention is directed, inter alia, to improved synthetic methods for producing 2-alkynyladenosine derivatives that provide higher yields and require less chromatographic purification than prior art methods, using alternative reagents and steps.

In another embodiment, the invention is directed to methods for preparing 2-iodoadenosine-5'-N-ethyluronamide, comprising the steps of:

providing 2-iodoadenosine;

protecting the hydroxyl groups of said 2-iodoadenosine with an acetonide group;

oxidizing the primary alcohol of said acetonide-protected 2-iodoadenosine to an acid derivative of said acetonide-protected 2-iodoadenosine;

converting said acid derivative to an N-ethylamide derivative of said acetonide-protected 2-iodoadenosine; and deprotecting said N-ethylamide of said acetonide-protected 2-iodoadenosine to form said 2-iodoadenosine-5'-N-ethyluronamide.

In other embodiments, the invention is directed to methods for preparing compounds of formula B:

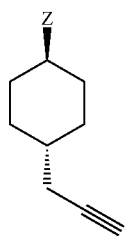

wherein Z is —CH$_2$C(═O)R, where R is a C$_1$ to C$_5$ alkyl, comprising the steps of providing 1,4-methanol cyclohexane;

preparing a mono-tosyl derivative of said 1,4-methanol cyclohexane;

preparing an acetylide-substituted compound of the formula:

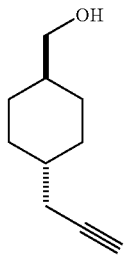

from said mono-tosyl derivative of said 1,4-methanol cyclohexane; and converting said acetylide-substituted compound to a compound of formula B:

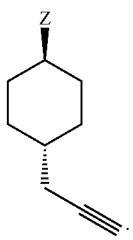

In yet other embodiments, the invention is directed to methods for preparing ds of formula B:

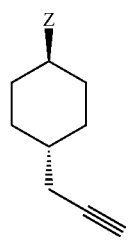

wherein Z is —C(=O)OR, where R is a $C_1$ to $C_5$ alkyl, comprising the steps of:

providing 1,4-methanol cyclohexane; and preparing a mono-tosyl derivative of said 1,4-methanol cyclohexane;

preparing an acetylide-substituted compound of the formula:

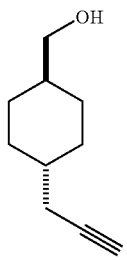

from said mono-tosyl derivative of said 1,4-methanol cyclohexane;

oxidizing said acetylide-substituted compound using radical oxidation; and esterifying said product of said oxidation to a compound of formula B:

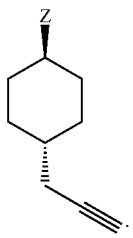

In one preferred embodiment, the 2-iodoadenosine-5'-N-ethyluronamide is prepared from 2-iodoadenosine.

In another preferred embodiment, the compound of formula B is prepared from 1,4-methanol cyclohexane.

The term "stereoisomers," as used herein, refers to compounds that have identical chemical constitution, but differ as regards the arrangement of the atoms or groups in space. It is understood that compounds of formula A may include one or more asymmetric carbons, and that formula A encompasses all possible stereoisomers and mixtures thereof, as well as racemic modifications, particularly those that possess the activities discussed herein. Compounds prepared by the present methods may be isolated in optically active or racemic forms. Thus, all chiral, diastereomeric, racemic forms and all geometric isomeric forms of a structure are intended, unless the specific stereochemistry or isomeric form is specifically indicated. Stereoisomers of the compounds of formula A can be selectively synthesized or separated in pure, optically-active form using conventional procedures known to those skilled in the art of organic synthesis. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

"Pharmaceutically acceptable salt," as used herein with respect to the compounds of the invention, refer to derivatives of the disclosed compounds wherein the parent compound of formula A is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

"$C_1$-$C_5$ alkyl," as used herein, refers to an optionally substituted, saturated straight, branched, or cyclic hydrocarbon having from about 1 to about 5 carbon atoms (and all combinations and subcombinations of ranges and specific numbers of carbon atoms therein), include, but are not limited to, methyl, ethyl, n-propyl, isopropyl, n-butyl, isobutyl, t-butyl, n-pentyl, cyclopentyl, isopentyl and neopentyl.

Scheme A: Synthesis of 2-IodoNECA

One of the requirements of the methods of the invention involves providing the compound 2-iodoNECA. This compound may be prepared in four steps as depicted in Scheme A.

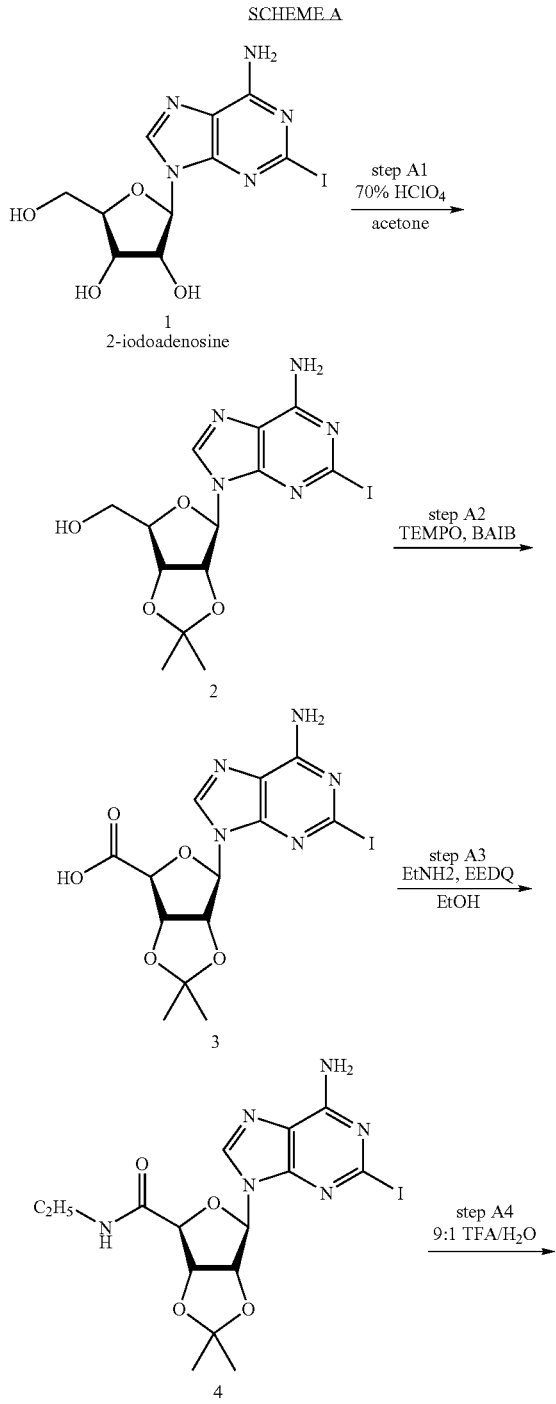

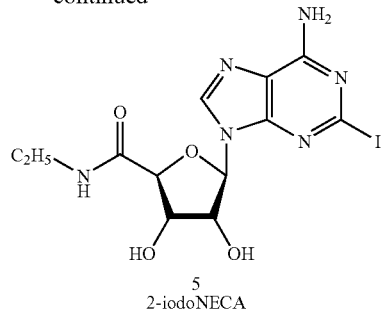
5
2-iodoNECA

Another method of preparing 2-iodoNECA is described in G. Cristalla et al., *J. Med. Chem.* 1992, 35:2363-68.

The starting material in Scheme A, 2-iodoadenosine (1), is commercially available from such sources as Toronto Research Chemicals. 2-Iodoadenosine may be synthesized by the method described in Matsuda et al., *J. Med. Chem.*, 1992, 35:241-252 and Nair et al., *Synthesis*, 1982, 670-672.

In Step A1, 2-iodoadenosine (1) is converted to its protected form (2), preferably its acetonide-protected form, by protecting the hydroxyl groups at 2' and 3' carbons on the ribose ring. This protection may be accomplished, for example, using 70% perchloric acid, methanesulfonic acid, p-toluenesulfonic acid or other sulfonic acids in excess acetone solvent or mixtures including acetone solvent. This step may be carried out for one hour to five hours at room temperature. The acid may be neutralized with, for example, aqueous sodium carbonate. The product (2) may be extracted in dichloromethane, for example, by concentrating the dichloromethane to solid and drying under vacuum, for example, at 40° C. This step typically provides yields as high as 90 to 93%. This improved approach to the rapid conversion of 2-iodoadenosine (1) to its acetonide form (2) proceeds cleanly and in high yield and requires no further purification. Previously reported procedures required chromatographic separations (WO 99/61054, Homma et al., *J. Med. Chem.* 1992, 35, 2881-2890).

In Step A2, the primary alcohol (2) is oxidized to the acid (3). This step may be carried out in about 8 to 24 hours obtaining high yields with simple isolation. This may be accomplished by radical oxidation, such as, for example, the use of bis-acetoxyiodobenzene with 2,2,6,6-tetramethyl piperidinyloxy free radical (TEMPO) (Epp, J. G. and Widlanski, T. S., *J. Org. Chem.* 1999, 64, 293), hypervalent iodine species, derivatives of TEMPO, including 4-benzyloxy derivative of TEMPO and the like. The reaction may be carried out in solvent, such as acetonitrile, by mixing the components at ambient temperatures for about 3 hours, cooling to about 0° C., filtering the resulting solids and washing with cold solvent and then drying under vacuum under elevated temperatures, for example, 50° C. for about 8 to 18 hours. Typical yields are as high as 80%. Conventional oxidation procedures using permanganate require long reaction times (U.S. Pat. No. 5,593,975) or have issues with competing oxidation at the 2-iodo position (Homma et al., *J. Med. Chem.*, 1992, 35, 2881-2890). Conventional oxidation procedures using Ru(III) catalyst result in lower yields and require chromatographic purification (Homma et al., *J. Med. Chem.*, 1992, 35, 2881-2890).

In Step A3, the acid (3) is converted to the N-ethylamide (4), preferably in a one pot reaction. Conventional activation methods use acid chloride. In certain embodiments, the acid may be activated as a succinimide derivative using a carbodiimide, such as N-ethyl-dimethylaminopropylcarbodiimide (EDC). The activated acid may then be treated with an excess of ethylamine to afford the amide in good yield and reasonable purity. In a preferred embodiment, Step A3 may be carried out by activating the acid using 2-ethoxy-1-ethoxycarbonyl-1,2-dihydroquinoline (EEDQ), for example, by mixing at about 35° C. for about 3 hours and then cooling to about 5 to 10° C. The reaction solution may then be directly treated with ethanol and saturated with ethylamine, to afford the N-ethylamide product (4) in high purity and yield after recrystallization. The recrystallization may be carried out, for example, by first distilling the crude product (4) to a minimum volume, dissolving the residue in dichloromethane, washing with acid and base, exchanging the dichloromethane with ethanol, cooling to 0° C. for 2 to 5 hours, filtering the product and drying at about 40° C. under vacuum for 12 to 24 hours. Typical yields are in the range of 65 to 70%. Preferably, the ethylamine is added as a 4 to 8 M solution in ethanol to the reaction mixture and stirred, for example, for about 16 hours. Alternatively, the reaction mixture may be saturated with gaseous ethylamine.

In step A4, the product (4) may be deprotected using a suitable acid, for example, trifluoroacetic acid/water or formic acid/water, to produce the key intermediate, 2-iodoN-ECA (5), as a pure powder that may be used directly in subsequent steps. This deprotection may be accomplished by mixing the reactants for about 3 to 5 hours. The compound 5 may be extracted, for example, by cooling the mixture to about 10° C. and adding to solvent, such as methyl tert-butyl ether (MTBE), stirring for about 2 hours after the complete addition of the solvent, filtering, washing with solvent and drying under vacuum at about 40° C. Suitable acids include, for example, mineral and organic acids, with organic acids being preferred. Suitable acids include, for example, hydrochloric acid, trifluoroacetic acid and formic acid, with trifluoroacetic being preferred. The quantity of acid employed to deprotect the compound 4 may vary depending, for example, on the particular acid employed, and the particular compound 4 involved. Generally speaking, a large excess of acid may be employed, as it is used as the solvent for the reaction. By way of general guidance, the deprotection of compound 4 may be conducted over a wide range of temperatures. Preferably, the reaction is conducted at a temperature and for a time sufficient to form the compound of formula 5. The particular temperatures and times may vary, depending, for example, on the particular compound 4 and acid involved, as well as the particular solvent employed. In preferred form, the deprotection of compound 4 may be conducted at a temperature of from about 10 to about 35° C., and all combinations and subcombinations of temperature ranges therein. More preferably, the deprotection of compound 4 may be conducted at about room temperature. The yields from this step are typically in the range of 90 to 95%.

The compound of formula 5 has been obtained in 62% overall yield from compound 1 with no chromatographic purification, as compared to a reported 30% yield for the previous method (WO 00/44763).

Scheme B1: Synthesis of cyclohexane-containing acetylene, where Z is —CH$_2$OC(=O)R (where R is C$_1$-C$_5$ alkyl)

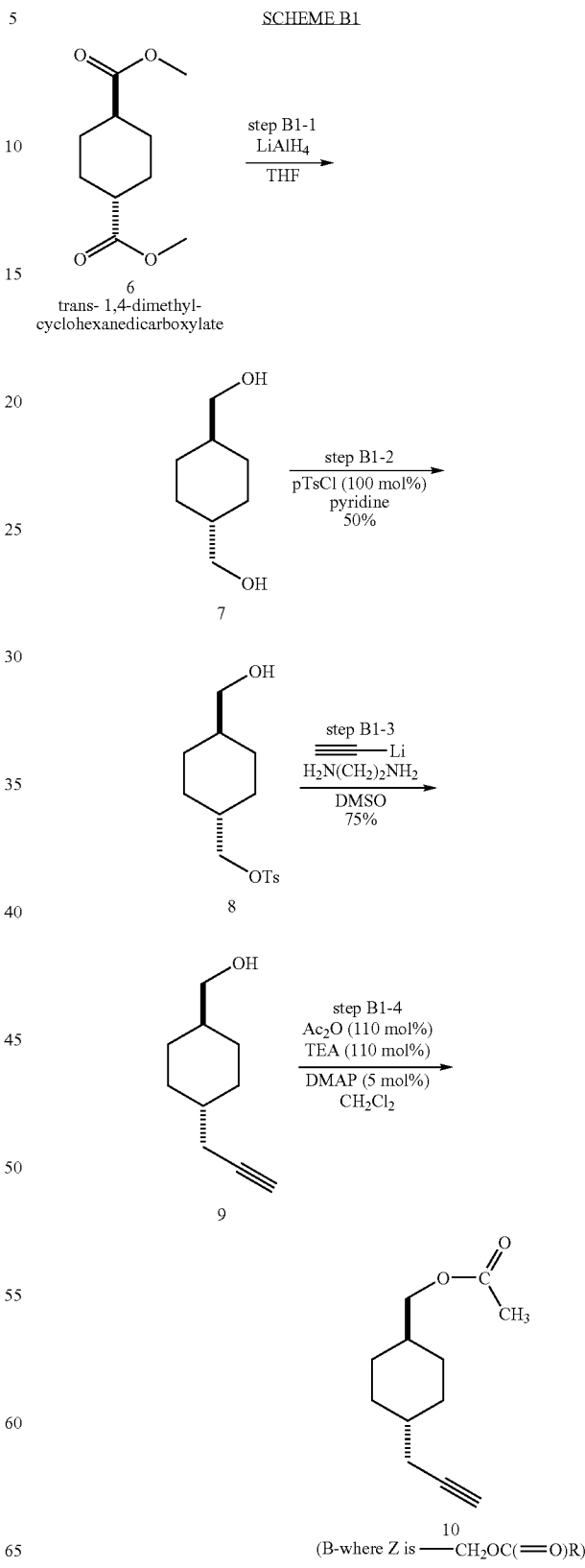

Scheme B2: Synthesis of cyclohexane-containing acetylene, where Z is —C(=O)OR (where R is $C_1$-$C_5$ alkyl)

SCHEME B2

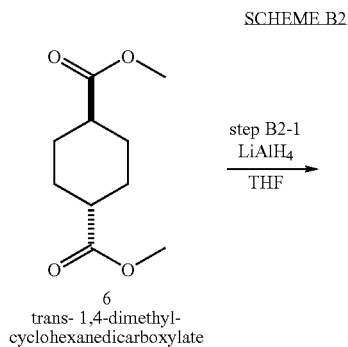

6
trans-1,4-dimethyl-cyclohexanedicarboxylate step B2-1
LiAlH$_4$
THF

7 step B2-2
pTsCl (100 mol%)
pyridine
50%

8 step B2-3
≡—Li
H$_2$N(CH$_2$)$_2$NH$_2$
DMSO
75%

9 step B2-4
TEMPO (20 mol %)
BAIB (220 mol%)
1/1 CH$_3$CN/H$_2$O

11 step B2-5
conc. HCl
CH$_3$OH

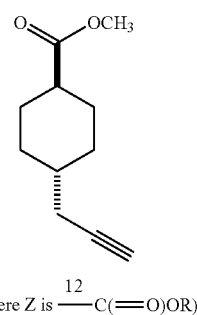

12
(B-where Z is —C(=O)OR)

Synthesis of the other key intermediates, the alkyne esters (10) and (12), is also improved over conventional procedures.

The starting material in Schemes B1 and B2, pure trans-cyclohexanedicarboxylic acid dimethyl ester (6), preferably containing less than about 0.2% by weight of the cis isomer, is commercially available from such sources as Aldrich.

The pure trans-diol (7) may be readily obtained by reducing the diester (6) to the diol with a reducing agent, such as, for example, lithium aluminum hydride (Step B1-1 or B2-1). The diester (6) is generally added to the solution of reducing agent at a rate determined by keeping the temperature of the solution between −10° C. and 25° C., preferably below 10° C. Other suitable reducing agents for producing pure trans-diol include, for example, borane and alane agents capable of reducing esters to alcohols. In certain preferred embodiments, commercially-available diol (7) at 98% trans isomer may be recrystallized from 2-ethoxyethylacetate to levels of greater than 99.5% pure trans isomer.

In Steps B1-2 and B2-2, pure mono-tosyl derivative (8) may be prepared and isolated without additional chromatographic purification. Residual diol starting material (7) may be removed by the aqueous workup and the ditosyl product removed through selective precipitation with methanol leaving the pure mono-tosyl derivative (8) in solution. Simple evaporation afforded the desired product (8) in pure form in 53% yield. This contrasts to the reported two-step procedure that afforded the protected mono-tosyl derivative in 51% yield after two chromatographic purifications (Rieger, J. M., Brown, M. L., Sullivan, G. W., Linden, J., and MacDonald, T. L., *J. Med. Chem.*, 2000, 44, 531-539), or in 35% yield after use of the single-step procedure (WO 00/44763).

It has been reported that the acetylide substitution on the tosylate is problematic, requiring a large excess of reagent with long reaction times, or the use of a protected intermediate with heating (Rieger, J. M., Brown, M. L., Sullivan, G. W., Linden, J., and MacDonald, T. L., *J. Med. Chem.*, 2000, 44, 531-539). Steps B1-3 and B2-3 of the invention using lithium acetylide-ethylene diamine complex and dimethylsulfoxide (DMSO) are rapid, producing high yields (90%), requiring no steps of heating, further purification or deprotection to generate the product alcohol (9).

For cyclohexane-containing acetylene compound where Z is —C(=O)OR (where R is $C_1$-$C_5$ alkyl) (Scheme B2), compound 9 is oxidized in step B2-4 using standard Jones oxidation conditions. Oxidation of the hydroxyl of hydroxylacetylene species using standard Jones oxidation conditions has been reported to afford 70-75% yields (Rieger, J. M., Brown, M. L., Sullivan, G. W., Linden, J., and MacDonald, T. L., *J. Med. Chem.*, 2000, 44, 531-539; WO 00/44763). Use of the TEMPO/bis-acetoxyiodobenzene (BAIB) in step B2-4 provides mild conditions for carrying out this transformation quickly (about 3 hours) and cleanly, in high isolated yields (95%).

In step B2-5, the carboxylic acid (11) may be converted to the desired ester (12) by a simple Fisher esterification reaction using a suitable alcohol (methanol for compound (12) or ethanol or 1-propanol), and catalyst, such as concentrated sulfuric acid, hydrochloric acid, anhydrous hydrogen chloride, p-toluenesulfonic acid and acid form of an ion exchange resin, followed by distillation, to produce the product (12) in good yield and purity without the use of expensive reagents like trimethylsilydiazomethane. This improved synthesis affords the desired ester-alkyne in four steps in 40% overall yield with no chromatographic purifications. This contrasts to the prior art syntheses that proceeded in four steps with a 22% yield after three column chromatography steps (Rieger, J. M., Brown, M. L., Sullivan, G. W., Linden, J., and MacDonald, T. L., *J. Med. Chem.*, 2000, 44, 531-539) or in six steps with a 28% overall yield with four chromatographic purifications (WO 00/44763).

In step B1-4, trans-4-(2-propynyl)-cyclohexylmethanol 9 is converted to its acetoxymethyl derivative 10. Compound 9 is acetylated with acetic anhydride/triethylamine using 4,4-dimethylaminopyridine catalysis to afford the desired acetoxymethyl derivative 10.

Scheme C1: Cross-coupling of product of Scheme B1 with product of Scheme A to produce the Compound of Formula A where Z is —CH$_2$C(═O)R (where R is C$_1$-C$_5$ alkyl)

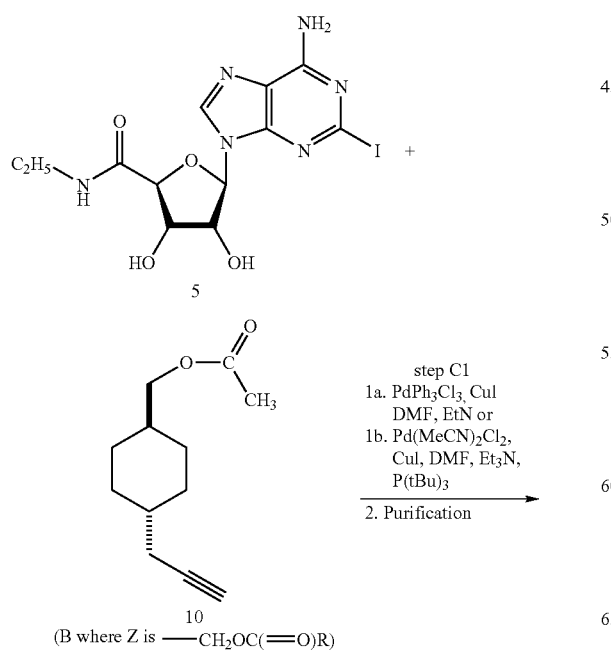

Scheme C2: Cross-coupling of product of Scheme B2 with product of Scheme A to produce the Compound of Formula A where Z is —C(═O)OR (where R is C$_1$-C$_5$ alkyl)

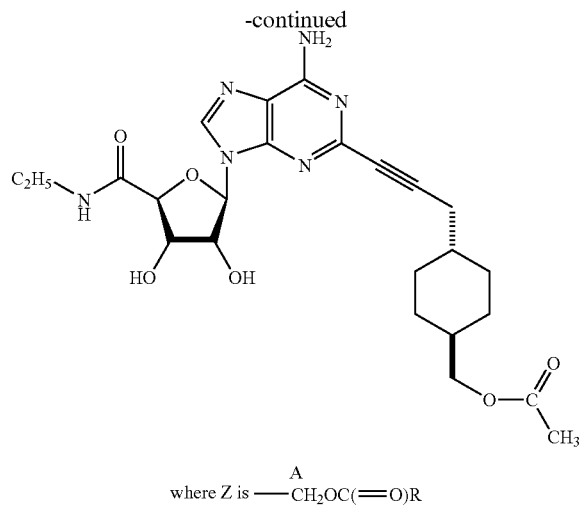

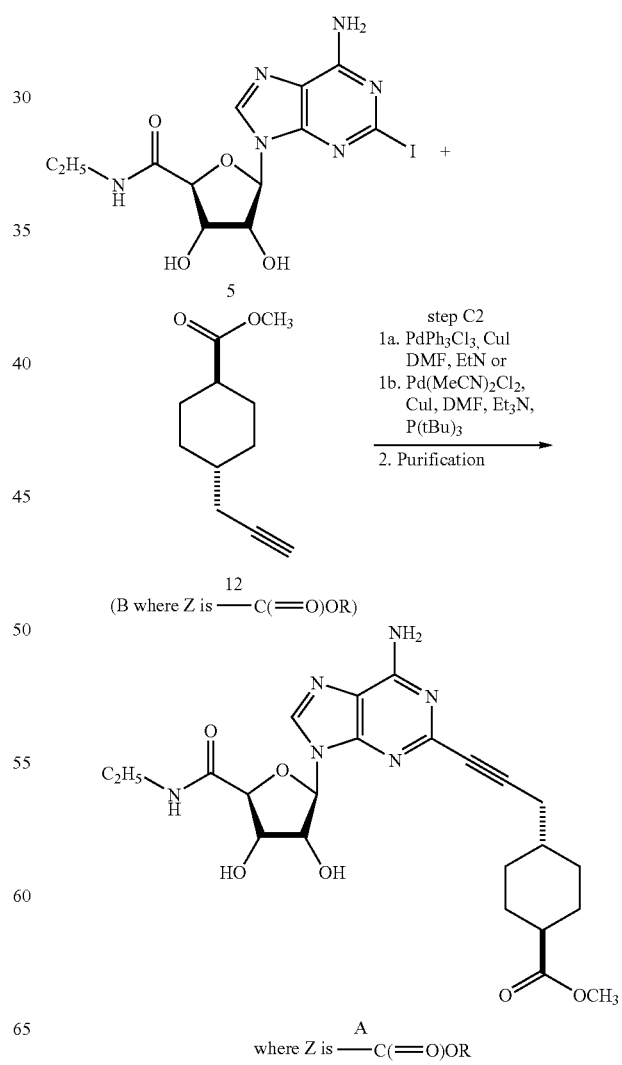

Compounds of formula A of the invention may be produced by the Sonagashira cross-coupling of either compound 10 with compound 5 (Scheme C1) to produce Compound A where Z is —CH$_2$C(=O)R, or compound 12 with compound 5 (Scheme C2) to produce Compound A where Z is —C(=O) OR. Generally, the halide-containing compound (either compound 10 or compound 12) and alkyne (for example, in 50% excess) may be dissolved in an appropriate anhydrous solvent, such as dimethyl formamide or N-methylpyrrolidine, under inert headspace, preferably nitrogen or argon. The copper iodide is added, followed by the palladium catalyst, preferably bis-triphenylphosphine palladium dichloride, maintaining the inert headspace. The reaction is stirred at ambient temperatures for about 2 to 5 hours, preferably about 2 hours, monitoring for disappearance of the aryl halide. When the aryl halide has been consumed, the solvent may be replaced by dichloromethane, the solution washed with EDTA to remove copper, dried, filtered and concentrated. The residue may be purified by flash chromatography and/or recrystallization.

The conditions for the Sonagashira coupling may be modified by the use of palladium bis-triphenylphosphine dichloride in triethylamine/dimethylformamide with no added phosphine or other cosolvent. This allows the reaction to proceed at room temperature to completion in 2 hours, as opposed to heating overnight as in prior art methods. Yields after flash chromatographic purification were 76%, as opposed to a reported 24% or 60% (Rieger, J. M., Brown, M. L., Sullivan, G. W., Linden, J., and MacDonald, T. L., *J. Med. Chem.*, 2000, 44, 531-539; WO 00/44763). Even if a highly purified form is desired, preparative HPLC purification only lowers the yields to 71%.

Thus, the methods of the invention produce the desired final product in a highly pure form, preferably with <0.2% contamination by the cis-isomer impurity, in ten steps with one chromatographic purification, in an overall yield of 17.6%. All of the reported steps are amenable to significant scale-up to relevant manufacturing scales. This contrasts with prior art methods, which afford a 1.6% overall yield in a similar number of steps (Rieger, J. M., Brown, M. L., Sullivan, G. W., Linden, J., and MacDonald, T. L., *J. Med. Chem.*, 2000, 44, 531-539), or a 5% overall yield with added steps (WO 00/44763)). In each case, a significant number of chromatographic purifications were required, which creates significant issues in scaling up to a relevant manufacturing scale.

In connection with the preparation of adenosine derivatives, the methods of the present invention may offer improved yields, purity, ease of preparation and/or isolation of intermediates and final product, and more industrially useful reaction conditions and workability over prior art methods of preparation. The present methods are particularly useful for the preparation of adenosine derivatives on a large scale, including commercial scale, for example, from multi-kilogram to ton quantities or more of adenosine derivative. Specifically, isolation and/or purification steps of intermediates to the adenosine derivatives may be advantageously substantially or completely avoided using the methods of the present invention. The present methods may be particularly advantageous in that the adenosine derivatives may be obtained in substantially pure form. The term "substantially pure form", as used herein, means that the adenosine derivative prepared using the present processes may preferably be substantially devoid of organic impurities. The term "organic impurities", as used herein, refers to organic materials, compounds, etc., other than the desired product, including, for example, the cis-isomer of compound of formula A, that may be typically associated with synthetic organic chemical transformations including, for example, unreacted starting reagents, unreacted intermediate compounds, and the like. In preferred form, the present processes may provide adenosine compounds that are at least about 75% pure, as measured by standard analytical techniques such as, for example, HPLC. Preferably, the adenosine derivatives prepared using the present methods may be at least about 80% pure, with a purity of at least about 85% being more preferred. Even more preferably, the adenosine derivatives prepared using the present methods may be at least about 90% pure, with a purity of at least about 95% being more preferred. In particularly preferred embodiments, the adenosine derivatives prepared using the present methods may be more than about 95% pure, with a purity of about 99.8% being even more preferred, and with a purity of about 100% being especially preferred.

If a salt of the compound of formula A is desired, a suitable acid may be added followed by cooling and seeding of the resultant solution to provide the crystalline salt. Preferably, the acid chosen will be able to form the salt without affecting the integrity of the target compound. Thus, mild acids, such as sulfonic acids, are preferred. In particular, methane sulfonic acid, benzenesulfonic acid, toluenesulfonic acid, hydroxyethanesulfonic acid, camphorsulfonic acid, and other sulfonic acids may prepare suitable crystalline salts. A particularly preferred acid is methane sulfonic acid. It will be appreciated, however, that numerous other salts are possible, when an anhydrous form of the acid is available. For example, mineral acids, such as hydrochloric, hydrobromic, phosphoric, sulfuric, or nitric acid may be used to prepare suitable crystalline salts. Other organic acids, such as fumaric, succinic, oxalic, citric, and the like, may be used to prepare suitable crystalline salts provided that they are sufficiently acidic to protonate the basic moiety of compound of formula A.

Under appropriate conditions, however, other solvents may be used to prepare crystalline salts of formula A, such as ester solvents, including, but not limited to ethyl acetate, propyl acetate, isopropyl acetate, isobutyl acetate, ethyl propionate, propyl propionate, isopropyl propionate; ether solvents, including, but not limited to t-butyl methyl ether, tetrahydrofuran, ethyl ether, isopropyl ether, butyl ether; and aromatic solvents, including, but not limited to toluene and anisole. Other solvents will be readily understood to those of ordinary skill in the art. Filtration and washing of the product, preferably with additional crystallization solvent, affords the compound of formula A.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

The reactions of the synthetic methods described and claimed herein may be carried out in suitable solvents which may be readily selected by one skilled in the art of organic synthesis. Generally, suitable solvents are solvents which are substantially non-reactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction, suitable solvents for a particular work-up following the reaction may be selected. Suitable solvents, as used herein may include, by way of example and without limitation, chlorinated solvents, hydrocarbon solvents, aromatic solvents, ether solvents, protic solvents, polar aprotic solvents, and mixtures thereof.

Suitable halogenated solvents include, but are not limited to carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable hydrocarbon solvents include, but are not limited to alkane or aromatic solvents such as cyclohexane, pentane, hexane, toluene, cycloheptane, methylcyclohexane, heptane, ethylbenzene, m-, o-, or p-xylene, octane, indane, nonane, benzene, ethylbenzene, and m-, o-, or p-xylene.

Suitable ether solvents include, but are not limited to dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol diisopropyl ether, anisole, or t-butyl methyl ether.

Suitable protic solvents include, but are not limited to water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, and glycerol.

Suitable aprotic solvents include, but are not limited to dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile (ACN), dimethylsulfoxide (DMSO), propionitrile, ethyl formate, methyl acetate, hexachloroacetone, acetone, ethyl methyl ketone, ethyl acetate, isopropyl acetate, t-butyl acetate, sulfolane (tetramethylene sulfone), N,N-dimethylpropionamide, nitromethane, nitrobenzene, and hexamethylphosphoramide.

The invention is further described in the following examples. All of the examples are actual examples. These examples are for illustrative purposes only, and are not to be construed as limiting the appended claims.

EXAMPLES

Example 1

Synthesis of [(1R,2R,4R,5R)-4-(6-amino-2-iodopurin-9-yl)-7,7-dimethyl-3,6,8-trioxabicyclo[3.3.0]oct-2-yl]methan-1-ol (Compound 2)

To a suspension of 2-iodoadenosine 1 (10.0 g, 25.4 mmol) in acetone (200 ml) cooled to 0° C. was added dropwise 70% perchloric acid (4.0 mL), resulting in an exotherm of about 5° C. The resultant colorless solution was allowed to warm to room temperature over 30 minutes, then stirred for a further 45 minutes. 1M $Na_2CO_3$ (50 mL) was added, resulting in solids precipitating. This was followed by the careful portion-wise addition of water (300 mL) with stirring until all solids had dissolved. The mixture was extracted with three portions of $CH_2Cl_2$. The combined organics were washed with brine, dried ($Na_2SO_4$), filtered, and evaporated to afford Compound 2 (10.26 g, 93%) as a colorless solid. $^1$H-NMR (600 MHz, DMSO $d_6$): 1.32 (s, 3H), 1.54 (s, 3H), 3.54 (m, 2H), 4.19 (m, 1H), 4.93 (dd, 1H), 5.05 (t, 1H), 5.27 (dd, 1H), 6.05 (d, 1H), 7.74 (bs, 2H), 8.28 (s, 1H); $^{13}$C-NMR (150 MHz, DMSO $d_6$): 25.45, 27.08, 85.69, 86.09, 88.44, 92.59, 114.92, 120.39, 142.47, 151.08, 157.20, 173.14. LRMS (ES): m/z=434.0 (M+H, 100%).

Example 2

Synthesis of 1'-deoxy-1'-(6-amino-2-iodo-9H-purin-9-yl)-2',3'-O-isopropylidene-β-D-ribofuranuronic acid (Compound 3)

To a solution of Compound 2 (10.0 g, 23.1 mmol) in $CH_3CN$ (200 mL) and water (50 mL) cooled to 0° C. was added iodobenzene diacetate (16.4 g, 50.8 mmol) and TEMPO (0.72 g, 20 mmol). The mixture was stirred at 0° C. for 30 minutes, then allowed to warm to room temperature and stirred for 22 h. The solvents were evaporated and the resulting residue was triturated with n-heptane (400 mL) overnight. The solids were filtered, washed with n-heptane and dried in vacuo to afford Compound 3 (9.80 g, 95%) as an off-white solid.

$^1$H-NMR (600 MHz, $CD_3OD$): 1.45 (s, 3H), 1.65 (s, 3H), 4.78 (d, 1H), 5.50 (d, 1H), 5.67 (dd, 1H), 6.31 (s, 1H), 8.14 (s, 1H); $^{13}$C-NMR (150 MHz, $CD_3OD$): 25.45, 27.08, 85.69, 86.09, 88.44, 92.59, 114.92, 120.39, 142.47, 151.08, 157.20, 173.14. LRMS (ES): 448.0 (M+H, 100%).

Example 3

Synthesis of N-ethyl-1'deoxy-1'-(6-amino-2-iodo-9H-purin-9-yl)-2',3'-O-isopropylidene-β-D-ribofuranuronamide (Compound 4)

To a solution of Compound 3 (8.0 g, 17.9 mmol) in 50% ethanol/$CH_2Cl_2$ (160 mL) was added 2-ethoxy-1-ethoxycarbonyl-1,2-dihydroquinoline (EEDQ) (4.65 g, 18.8 mmol) as a single portion. The mixture was stirred at room temperature for 24 hours. Ethanol (80 mL) was added and ethylamine gas (~45 g) bubbled through the reaction solution over 4 hours. The reaction was stirred at room temperature for 20 hours after which the solvents were evaporated. The resulting solids were dissolved in $CH_2Cl_2$ and washed successively with 0.1 M HCl and 1M $Na_2CO_3$. The organics were dried ($Na_2SO_4$), filtered, and evaporated to afford Compound 4 as a pale yellow solid which was recrystallized from $CH_2Cl_2$/hexanes to afford Compound 4 (6.0 g, 71%) as a white solid, m.p. 204-206° C.; $^1$H-NMR (600 MHz, DMSO-$d_6$): 0.68 (t, 3H), 1.32 (s, 3H), 1.52 (s, 3H), 2.81 (m, 1H), 2.91 (m, 1H), 4.53 (s, 1H), 5.33 (m, 1H), 5.36 (m, 1H), 6.27 (s, 1H), 7.43 (t, 1H), 7.68 (s, 2H), 8.16 (s, 1H); $^{13}$C-NMR (150 MHz, DMSO-$d_6$): 14.07, 25.06, 26.61, 33.07, 83.15, 83.35, 112.77, 118.71, 120.68, 139.99, 149.31, 155.81, 167.92. LRMS (ES): m/z=475.0 (M+H, 100%).

Example 4

Synthesis of [(2S,3S,4R,5R-5-(6-amino-2-iodopurin-9-yl)-3,4-dihyroxyoxolan-2-yl]-N-ethylcarboxamide (Compound 5)

To a stirred solution of 10% aqueous trifluoroacetic acid (1100 mL) is added Compound 4 (80 g, 168 mmol) over 5 minutes with stirring. The solution was stirred for 1 hour at room temperature, and then concentrated under reduced pressure. The resulting brown oil was triturated with methyl tert-butyl ether (MTBE) to afford a solid which was filtered, rinsed with MTBE, and dried under vacuum to yield Compound 5 (72.7 g, 99%) as a white powder. $^1$H-NMR (600 MHz, DMSO-$d_6$): 1.05 (t, 3H), 3.24 (m, 2H), 4.17 (dd, 1H), 4.31 (d, 1H), 4.58 (dd, 1H), 5.91 (d, 1H), 7.74 (bs, 2H), 8.10 (t, 1H), 8.38 (s, 1H); $^{13}$C-NMR (150 MHz, DMSO-$d_6$): 14.78, 26.77, 33.47, 72.65, 72.94, 84.20, 119.16, 120.91, 149.84, 155.90, 169.00; LRMS (ES): m/z=435.1 (M+H, 100%)

Example 5

Synthesis of trans-[(4-hydroxymethyl)cyclohexyl]methan-1-ol (Compound 7)

To a suspension of lithium aluminum hydride (7.6 g, 0.2 mol) in anhydrous tetrahydrofuran (600 mL) cooled to 4° C. under a positive nitrogen pressure was added dropwise over 30 minutes a solution of trans-1,4-dimethyl-cyclohexanedicarboxylate 6 (20 g, 0.1 mol) in anhydrous tetrahydrofuran (400 mL) at a rate to maintain a temperature of <10° C. during addition. The reaction was stirred with cooling for a further 30 minutes, then allowed to warm to room temperature and stirred for 70 hours. The reaction was cooled to 4° C., and water (7.6 mL) added carefully, followed by 15% NaOH (7.6 mL), and water (22.8 mL). The mixture was allowed to gradually warm to room temperature, then stirred at room temperature for 5 hours. The resultant colorless suspension was filtered, and the filtrate concentrated to afford Compound 7 (13.0 g, 90%) as an off-white solid. $^1$H-NMR (400 MHz, CDCl$_3$): 0.83 (m, 4H), 1.26 (m, 2H), 1.72 (d, 4H), 3.19 (t, 4H), 4.34 (t, 2H); $^{13}$C-NMR (100 MHz, CDCl$_3$): 29.05, 40.63, 66.79.

Example 6

Synthesis of trans-[{(4-hydroxymethyl)cyclohexyl}methyl]-4-methylbenzenesulfonate (Compound 8)

To a solution of Compound 7 (100 g, 0.69 mol) in anhydrous pyridine (1 L) stirred at room temperature was added portionwise p-toluenesulfonylchloride (132 g, 0.69 mol). The reaction was stirred for 1 hour, over which time a colorless precipitate was observed to form. The reaction temperature was cooled to –10° C. and water (4 L total) added carefully, keeping the temperature <20° C. The mixture was extracted with CH$_2$Cl$_2$, washed with 3M HCl, dried (MgSO$_4$), filtered, and evaporated. The crude residue was triturated with anhydrous MeOH and the resulting solids were removed by filtration. The filtrate was evaporated to afford Compound 8 (110 g, 53%) as a pale yellow oil. $^1$H-NMR (400 MHz, CDCl$_3$): 0.91 (m, 4H), 1.37 (m, 1H), 1.58 (m, 1H), 1.75 (m, 4H), 1.84, (s, 1H), 2.42 (s, 3H), 3.39 (d, 2H), 3.80 (d, 2H), 7.34 (d, 2H), 7.75 (d, 2H); $^{13}$C-NMR (100 MHz, CDCl$_3$): 21.53, 28.32, 28.34, 37.22, 39.99, 68.07, 75.16, 127.73, 129.72, 132.85, 144.62.

Example 7

Synthesis of (4-prop-2-ynylcyclohexyl)methan-1-ol (Compound 9)

To a solution of Compound 8 (110 g, 0.37 mol) in DMSO (1.46 L) was added as a single portion, lithium acetylide/ethylenediamine complex (>90% purity, 101.4 g, 1.10 mol). The reaction was stirred at ambient temperature for 2 hours. Water (3.8 L) was then added cautiously over 35 minutes, maintaining a solution temperature <37° C. Methyl tert-butyl ether (MTBE) (3 L) was then added and the biphasic mixture stirred vigorously for 10 minutes. The organic phase was separated and the aqueous phase further extracted with MTBE. The combined extracts were washed with water, dried (MgSO$_4$), filtered, and evaporated to afford Compound 9 (50.3 g, 90%) as a pale yellow oil. $^1$H-NMR (400 MHz, CDCl$_3$): 0.96 (m, 4H), 1.41 (m, 2H), 1.82 (m, 4H), 1.94, (t, 1H), 2.07 (d of d, 2H), 2.16 (s, 1H), 3.39 (d, 2H); $^{13}$C-NMR (100 MHz, CDCl$_3$): 25.91, 29.04, 31.71, 37.04, 40.07, 68.23, 69.01, 83.24.

Example 8

Synthesis of trans-4-(2-propynyl)-cyclohexylmethanol acetate (Compound 10)

A solution of trans-4-(2-propynyl)-cyclohexylmethanol (Compound 9) (15 g, 98 mmol), triethylamine (TEA) (15.1 mL, 108 mmol), and 4-(N,N-dimethyl-amino)pyridine (DMAP) (0.6 g, 5 mmol) in dichloromethane (300 mL) was cooled to 2° C. with stirring under nitrogen. Acetic anhydride (Ac$_2$O) (10.2 mL, 108 mmol) was added dropwise, keeping temperature below 10° C. After 30 minutes stirring at ice bath temperature, the reaction was quenched with 10% potassium carbonate solution (300 mL). The layers were separated and the organic layer was washed successively with 1N HCl, water, and brine, dried over magnesium sulfate, filtered, and concentrated under vacuum to afford 20 g of product as a yellow oil which was distilled bulb to bulb under vacuum (0.5 torr, 70° C.) to afford the product (Compound 10) as a colorless oil (17 g, 89%). $^1$H-NMR (600 MHz, CDCl$_3$): 1.03 (m, 4H), 1.46 (m, 1H), 1.59 (m, 1H), 1.85 (dd, 4H), 1.89 (t, 1H), 2.05 (t, 3H), 2.11 (dd, 2H), 3.89 (d, 2H).

Example 9

Synthesis of 4-prop-2-ynylcyclohexane carboxylic acid (Compound 11)

To a suspension of Compound 9 (2.45 g, 16 mmol) in 50% acetonitrile/water (35 mL) cooled to 0° C. was added bis-acetoxy-iodobenzene (BAIB) (11.4 g, 35 mmol) and TEMPO (502 mg, 3.2 mmol). The reaction mixture was stirred at 0° C. for 1 hour, then for 90 minutes at room temperature. The solvents were evaporated, and the residue dissolved in 1/1 CH₃CN/H₂O (100 mL). Once again the solvents were evaporated, and this procedure repeated to remove iodobenzene as its azeotrope. The resulting Compound 11 (2.53 g, 95%) was obtained as a brown sticky solid that was not further purified but carried forward into the next step. $^1$H-NMR (600 MHz, CD₃OD): 1.13 (dq, 2H), 1.45 (dq, 2H), 1.48 (m, 1H), 1.93 (dd, 2H), 2.03 (dd, 2H), 2.12 (dd, 2H), 2.2-2.3 (m, 2H).

Example 10

Synthesis of methyl 4-prop-2-ynyl cyclohexanecarboxylate (Compound 12)

To a solution of Compound 11 (0.88 g, 5.29 mmol) in methanol (10 mL) was added concentrated HCl (0.5 mL) and the mixture stirred at room temperature for 2 hours. The solvents were evaporated and the residue dissolved in CH₂Cl₂, dried (Na₂SO₄), filtered, and evaporated to afford a pale yellow oil. The oil was purified by bulb-to-bulb distillation (140° C. at 500 mTorr) to afford Compound 12 (0.80 g, 84%) as a pale pink oil. $^1$H-NMR (600 MHz, CD₃OD): 1.13 (dq, 2H), 1.45 (dq, 2H), 1.48. (m, 1H), 1.94 (dd, 2H), 2.01 (dd, 2H), 2.12 (dd, 2H), 2.24 (t, 1H), 2.28 (m, 1H), 3.68 (s, 3H); $^{13}$C-NMR (150 MHz, CD₃OD): 26.55, 29.96, 32.48, 37.79, 44.31, 52.08, 70.57, 83.44; FTIR (KBr) 1743 (C=O), 2117 (C≡C), 2872, 2953 (C—H), 3314 cm$^{-1}$ (C≡C—H)

Example 11

1-[2-[3-[trans-4-[(Acetyloxy)methyl]cyclohexyl]-1-propynyl]-6-amino-9H-purin-9-yl]-1-deoxy-N-ethyl-β-D-ribofuranuronamide (Compound A where Z is —CH₂C(=O)CH₃)

To a stirred suspension of 1-(6-amino-2-iodo-9H-purin-9-yl)-1-deoxy-N-ethyl-β-D-ribofuranuronamide 5 (75 mg, 0.17 mmol) in dry dioxane (2 mL) was added trans-4-(2-propynyl)-cyclohexylmethanol acetate 10 (54 mg, 0.28 mmol), triethylamine (78 µL, 0.56 mmol), copper iodide (11.3 mg, 59 µmol), bis-acetonitrile palladium dichloride (11.8 mg, 45 µmol), and tri(tert-butyl)phosphine (10% in hexanes, 93 µL, 30 µmol). This was stirred for 20 hours at room temperature, then triethylamine (1 mL) was added and the solution heated to 50° C. for 5 hours. Dimethylformamide (2 mL) was added along with additional aliquots of cyclohexylmethanol acetate (100 mg), CuI (5 mg), Pd(MeCN)₂Cl₂ (10 mg), and tri(tert-butyl)phosphine (200 µL), and the heating continued for 26 hours. The solvents were removed under vacuum, and the residue dissolved in chloroform, washed with 0.01 M Na₂EDTA solution (2×50 mL) and brine, dried over sodium sulfate, filtered, and evaporated. The residue was purified by flash chromatography (95:5 dichloromethane/methanol) to afford the product (Compound A where Z is —CH₂C(=O)CH₃) as a brown solid (40 mg, 47%): $^1$H-NMR (600 MHz, DMSO-d₆): 1.01 (m, 4H), 1.06 (t, 3H), 1.48 (m, 2H), 1.8 (dd, 4H), 2.00 (s, 3H), 2.32 (d, 2H), 3.25 (m, 1H), 3.30 (m, 1H), 3.83 (d, 2H), 4.11 (t, 1H), 4.30 (d, 1H), 4.57 (m, 1H), 5.53 (d, 1H), 5.73 (d, 1H), 5.92 (d, 1H), 7.52 (bs, 2H) 8.41 (s, 1H), 8.73 (t, 1H); $^{13}$C-NMR (150 MHz, CD₃OD): 14.94, 25.67, 28.21, 31.30, 33.28, 36.38, 36.50, 68.52, 71.80, 73.11, 81.93, 84.38, 84.65, 87.64, 119.06, 141.45, 145.63, 148.95, 155.96, 169.17, 170.38; LRMS (ES): 501.2 (M+H, 100%).

Example 12

1-[2-[3-[trans-4-[(Acetyloxy)methyl]cyclohexyl]-1-propynyl]-6-amino-9H-purin-9-yl]-1-deoxy-N-ethyl-β-D-ribofuranuronamide (Compound A where Z is —CH₂C(=O)CH₃)

Alternatively, Compound A where Z is —CH₂C(=O)CH₃ may be obtained by the following procedure:

A flask is charged with Compound 5 (33 g, 76 mmol), Compound 10 (22.3 g, 115 mmol), dry dimethylformamide (330 mL), and triethylamine (115 mL) under a nitrogen atmosphere. The stirred solution is sparged with dry nitrogen for 15 minutes and then copper iodide (2.21 g, 11.6 mmol) and palladium bis(triphenylphosphine)dichloride (4 grams, 5.7 mmol) are added, maintaining nitrogen purge. The reaction is stirred at room temperature for 1.5 hours and concentrated under reduced pressure to produce a brown oil. This is redissolved in dichloromethane and washed with four portions of 0.1N EDTA solution. The organics are dried (Na₂SO₄), filtered, and concentrated under vacuum. The crude material is purified by flash chromatography (1-7% methanol gradient in dichloromethane) to afford Compound A where Z is —CH₂C(=O)CH₃ as a pale yellow solid.

Example 13

Synthesis of 4-{3-[6-amino-9-(5-ethyl carbamoyl-3,4-dihydroxy tetrahydrofuran-2-yl)₉H-purin-2-yl]prop-2-ynyl}cyclo hexanecarboxylic acid methyl ester (Compound A where Z is —C(=O)OCH₃)

A flask was charged with Compound 5 (33 g, 76 mmol), Compound 12 (20.7 g, 115 mmol), dry dimethylformamide (330 mL), and triethylamine (115 mL) under a nitrogen atmosphere. The stirred solution was sparged with dry nitrogen for 15 minutes and then copper iodide (2.21 g, 11.6 mmol) and palladium bis(triphenylphosphine)dichloride (4 grams, 5.7 mmol) were added, maintaining nitrogen purge. The reaction was stirred at room temperature for 1.5 hours and concentrated under reduced pressure to a brown oil. This was redissolved in dichloromethane and washed with four portions of 0.1N EDTA solution. The organics were dried (Na₂SO₄), filtered, and concentrated under vacuum. The crude material was purified by flash chromatography (1-7% methanol gradient in dichloromethane) to afford Compound A where Z is —C(=O)OCH₃ (28.1 grams, 76%) as a pale yellow solid.

Example 14

Purification of 4-{3-[6-amino-9-(5-ethyl carbamoyl-3,4-dihydroxy tetrahydrofuran-2-yl)-9H-purin-2-yl]prop-2-ynyl}cyclohexane carboxylic acid methyl ester (Compound A where Z is —C(=O)OCH₃)

Purification of Compound A where Z is —C(=O)OCH₃ was accomplished in two ways: preparative HPLC and recrystallization. Preparative HPLC was carried out on a Dynamax C-18 (8 µm, 60 A, 15×30 cm) using gradient of 25%-40% B over 60 minutes (A=0.05N ammonium acetate, pH=5.0; B=acetonitrile) with an injection solution of 22.8 g Compound A where Z is —C(=O)OCH₃ in 6 L of 25% acetonitrile in 0.05 N ammonium acetate. The eluent was monitored at 270 nM and product fractions isolated. The product fractions were combined and diluted with an equal volume of water. They were injected onto the same column running a gradient of 20%-80% B over 30 minutes (A=water;

B=acetonitrile) to remove salts. Product fractions were combined, frozen, and lyophilized to afford Compound A where Z is —C(=O)OCH$_3$ (21.4 g, 94%) as a flocculent white powder.

Crystallization were done from 10:1 2-propanol/methyl tert-butyl ether (MTBE). Compound A where Z is —C(=O)OCH$_3$ was dissolved in a minimum volume of hot 2-PrOH and MTBE added while hot. The solution was allowed to cool with stirring in a 0° C. bath. It was allowed to stand overnight at −8° C. and then filtered, washed with 1:1 2-PrOH/MTBE, followed by MTBE, and then dried under vacuum to afford Compound A where Z is —C(=O)OCH$_3$ as a white flowable powder. $^1$H-NMR (600 MHz, CD$_3$OD): 1.21 (t, 3H), 1.22 (dq, 2H), 1.48 (dq, 2H), 1.65 (m, 1H), 2.04 (dt, 4H), 2.34 (dt, 1H), 2.45 (d, 2H), 3.44 (dm, 2H), 3.69 (S, 3 h), 4.36 (dd, 1H), 4.50 (d, 1H), 4.74 (dd, 1H), 6.07 (d, 1H, 8.48 (s, 1H); $^{13}$C-NMR (150 MHz, CD$_3$OD): 14.78, 26.77, 33.47, 72.65, 72.94, 84.20, 119.16, 120.91, 149.84, 155.90, 169.00; LRMS (ES): 487.2 (M+H, 100%).

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The invention claimed is:

1. A method for preparing a compound of formula A:

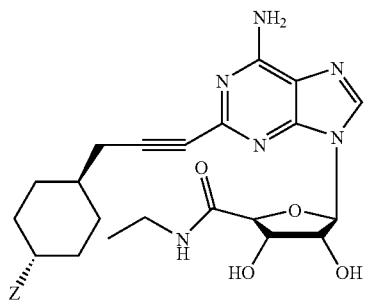

or a stereoisomer, pharmaceutically acceptable salt, hydrate, solvate, acid salt hydrate or isomorphic crystalline form thereof, the method comprising the step of:
(1) providing 2-iodoadenosine;
(2) protecting the hydroxyl groups of said 2-iodoadenosine with an acetonide group;
(3) oxidizing, via radical oxidation, the primary alcohol of said acetonide-protected 2-iodoadenosine to an acid derivative of said acetonide-protected 2-iodoadenosine;
(4) converting said acid derivative to an N-ethylamide derivative of said acetonide-protected 2-iodoadenosine;
(5) deprotecting said N-ethylamide of said acetonide-protected 2-iodoadenosine to form said 2-iodoadenosine-5'-N-ethyluronamide; and
(6) contacting said 2-iodoadenosine-5'-N-ethyluronamide with a compound of formula B in the presence of CuI and Pd(PPh$_3$)$_2$Cl$_2$:

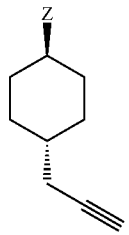

wherein
Z is —C(=O)OR, where R is a C$_1$ to C$_5$ alkyl.

2. The method according to claim 1, wherein Z is —C(=O)OCH$_3$.

3. The method according to claim 1, wherein said oxidizing step comprises the use of a mixture comprising bis-acetoxy-iodobenzene and 2,2,6,6-tetramethyl piperidinyloxy free radical (TEMPO).

4. The method according to claim 1, wherein said compound of formula B is prepared from 1,4-methanol cyclohexane.

5. The method according to claim 4, wherein said 1,4-methanol cyclohexane is prepared from a reaction mixture comprising trans-1,4-dimethyl-cyclohexanedicarboxylate.

6. The method according to claim 5, wherein said reaction mixture comprises less than about 0.2% by weight, based on the total weight of the 1,4-dimethyl-cyclohexanedicarboxylate, of cis-1,4-dimethyl-cyclohexanedicarboxylate.

7. The method according to claim 4, wherein said 1,4-methanol cyclohexane is prepared by a process comprising the step of reducing 1,4-dimethyl-cyclohexanedicarboxylate.

8. The method according to claim 4, further comprising the step of preparing the mono-tosyl derivative of said 1,4-methanol cyclohexane.

9. The method according to claim 8, further comprising the step of acetylide substitution of said tosyl derivative of the formula:

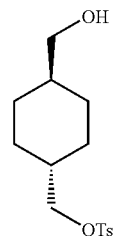

to form and acetylide-substituted compound of the formula:

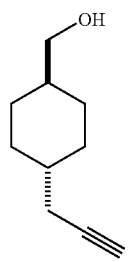

10. The method according to claim 9, further comprising the steps of oxidizing said acetylide-substituted compound and esterifying said product of said oxidation to a compound of formula B, where Z is —C(=O)OR.

* * * * *